(12) United States Patent  (10) Patent No.: US 6,455,865 B2
Egawa  (45) Date of Patent: Sep. 24, 2002

(54) TEST PIECE ANALYZING APPARATUS

(75) Inventor: Kouji Egawa, Kyoto (JP)

(73) Assignee: Kyoto Daiichi Kagaku Co., Ltd., Kyoto (JP)

( * ) Notice: Subject to any disclaimer, the term of this patent is extended or adjusted under 35 U.S.C. 154(b) by 0 days.

(21) Appl. No.: 09/845,895

(22) Filed: Apr. 30, 2001

Related U.S. Application Data

(62) Division of application No. 09/364,929, filed on Aug. 2, 1999, now Pat. No. 6,337,490.

(30) Foreign Application Priority Data

Aug. 6, 1998 (JP) .......................................... 10-236357
Aug. 6, 1998 (JP) .......................................... 10-236358
Aug. 6, 1998 (JP) .......................................... 10-236359

(51) Int. Cl.[7] .............................................. G01N 21/86
(52) U.S. Cl. ................................ 250/559.4; 250/559.11
(58) Field of Search ......................... 250/559.4, 559.44, 250/573, 578.1, 226, 216, 559.11; 356/239.1, 237.1, 239.2, 39

(56) References Cited

U.S. PATENT DOCUMENTS

| 5,184,359 A | 2/1993 | Tsukamura et al. .......... 128/760 |
| 5,339,829 A | 8/1994 | Thieme et al. ............... 128/760 |
| 5,523,055 A | 6/1996 | Hansen et al. ................ 422/58 |
| 6,276,366 B1 | 8/2001 | Fuchigami et al. .......... 131/280 |
| 6,381,356 B1 * | 4/2002 | Murakami et al. ......... 356/237.1 |

* cited by examiner

Primary Examiner—Que T. Le
(74) Attorney, Agent, or Firm—Merchant & Gould P.C.

(57) ABSTRACT

A test piece analyzing apparatus is provided which includes a releasably fixed absorbent member, a horizontally reciprocative pinching mechanism for simultaneously transferring a plurality of test pieces in a transfer direction, and an optical analyzing assembly provided with a primary illuminator and a secondary illuminator. The second illuminator serves to illuminate the bottom surface of the test piece.

6 Claims, 16 Drawing Sheets

TEST PIECE ANALYZING APPARATUS

This application is a divisional of application Ser. No. 09/364,929, filed Aug. 2, 1999, now U.S. Pat. No. 6,337,490, which application(s) are incorporated herein by reference.

BACKGROUND OF THE INVENTION

1. Field of the Invention

The present invention relates to a medical analyzing apparatus for automatically transferring and analyzing test pieces each of which is dipped in a fluid specimen such as urine or blood. In particular, the present invention relates to assemblies incorporated in the analyzing apparatus: an assembly for removing an excessive amount of specimen on a test piece, an assembly for transferring a plurality of test pieces simultaneously, and an assembly for analyzing test pieces by photometry.

2. Description of the Related Art

Conventionally, use has been made of a rectangular test piece carrying several test pads for performing medical checkup of a specimen such as urine or blood. Each of these test pads contains a certain reagent. Thus, when the test piece is dipped in the specimen, the test pads may change colors. By analyzing these changes in color by photometry, the medical conditions of the specimen are known.

For automatically performing the photometric analysis of a test piece dipped in a specimen, use may be made of a test piece analyzing apparatus. An example of conventional test piece analyzing apparatus includes a test piece transfer unit and a test piece analyzing unit. The test piece transfer unit serves to transfer a test piece dipped in the specimen to the test piece analyzing unit. At the analyzing unit, the specimen-wet test piece (simply called "wet test piece" hereinafter) is subjected to a predetermined photometric analysis. To this end, the conventional test piece analyzing unit may include an optical system for subjecting the wet test piece to an optical treatment and a driving mechanism for moving the optical system relative to the test piece.

Conventionally, the automatic transfer of a wet test piece may be performed in two ways. According to one of them, the wet test piece is caused to slide on a supporting member to be brought to the analyzing unit. According to the other way, the wet test piece is picked up by a holding mechanism to be moved in midair toward the analyzing unit.

Though there are some advantages, the former method is disadvantageous in that the wet test piece will contaminate the supporting member during the sliding transfer operation. By the latter method, more than one test piece cannot be transferred simultaneously, thereby reducing the operational efficiency.

For removing an excessive amount of the specimen on the test piece, a suction pump may conventionally be used together with an effluent bottle connected to the suction pump via a pipe. When the effluent bottle is full of the collected specimen, the user may empty the bottle and clean it for reuse.

However, the above manner is disadvantageous in the following points. First, the suction pump cannot be actuated without power supply. Second, the mechanical suction pump tends to make noises in use. Third, it is a troublesome job to clean the effluent bottle. Fourth, an additional inner space is needed within the analyzing apparatus for installing the suction pump and the effluent bottle, which may result in an increase in size of the analyzing apparatus.

The conventional test piece analyzing unit is also disadvantageous in the following points. As stated above, the test piece analyzing unit is provided with an optical system for subjecting a wet test piece to an optical treatment. More specifically, the optical system includes an illuminator for illuminating the wet test piece from above, and a light receiving device for detecting light reflected on the wet test piece. Based on the detected reflection light, the locations of the test pads on the test piece are determined, and the color changes of the test pads are evaluated.

In the above arrangement, however, it is difficult to accurately determine the locations of the test pads on the test piece. This is because when the test piece is wet with the specimen, it tends to become difficult to distinguish light reflected on a test pad from light reflected on a portion of the test piece at which no test pad is provided.

SUMMARY OF THE INVENTION

The present invention has been proposed under the above circumstances and its object is to reduce or even eliminate the problems described above.

For attaining this object, the present invention adopts the following technical measures.

According to a first aspect of the present invention, there is provided a fluid absorber for removing an excessive amount of specimen on a test piece comprising:

an absorbent member for absorbing the excessive amount of specimen; and a holding member for supporting the absorbent member, so that the absorbent member comes into contact with the test piece.

The absorbent member may be arranged to come into contact with the test piece after the test piece is slidably moved by a predetermined distance.

The absorbent member may be made of an absorbent fiber, a porous resin, a macromolecular absorber, a sponge and the like.

Preferably, the absorbent member may be supported by the holding member in a replaceable manner.

The fluid absorber further comprises a casing for accommodating the absorbent member, wherein the casing is supported by the holding member in a replaceable manner.

According to a second aspect of the present invention, there is provided a test piece transfer assembly for transferring test pieces from a first waiting region to a second waiting region, the test piece transfer assembly comprising:

a test piece holding section extending from the first waiting region to the second waiting region, the test piece holding section being arranged to hold a predetermined number of plural test pieces disposed at regular intervals; and a horizontally reciprocative pinching mechanism arranged to simultaneously hold the predetermined number of test pieces in midair and release the predetermined number of test pieces after the test pieces are advanced by the regular interval.

The pinching mechanism may comprises:

a plurality of test piece holding members each arranged to pinch, lift, lower and release a test piece;

a first actuating mechanism arranged to cause each of the test piece holding members to pinch, lift, lower and release a test piece;

a second actuating mechanism arranged to cause the test piece holding members to advance by the regular interval when the test pieces are lifted, while also being arranged to cause the test piece holding members to regress by the regular interval after the test pieces are released.

The test piece transfer assembly may further comprise a reciprocative casing and a rod supported by the reciprocative casing for pivotably holding the test piece holding members disposed at the regular intervals, wherein each of the test piece holding members includes a first piece and a second piece, the first piece releasably engaging with a surface of a relevant test piece, the second piece releasably engaging with another surface of the relevant test piece.

The first and the second pieces of each test piece holding member may be urged in a predetermined direction by elastic members, the first and the second pieces of each test piece holding member being selectively brought into an open state and a closed state.

The first actuating mechanism may include a rotation shaft, a cam secured to the rotation shaft, and a cam follower associated with the cam for actuating the test piece holding members.

The cam may have a quarter-circular configuration.

The second actuating mechanism may include a protruding piece movable about an axis, and a swing arm formed with a guiding groove for slidably receiving the protruding piece.

The test piece holding section may be provided with a pair of rails formed with hollows for positioning the test pieces.

The test piece transfer assembly may further comprise a test piece discarding opening adjacent to the test piece holding section.

According to a third aspect of the present invention, there is provided an optical analyzing assembly for a test piece having an obverse surface and a reverse surface, the obverse surface carrying at least one test pad, the analyzing assembly comprising:

a first illuminator for illuminating the obverse surface of the test piece;

a light receiving device for receiving light reflected on the obverse surface of the test piece; and a second illuminator for illuminating the reverse surface of the test piece for locating the test pad;

wherein the light receiving device also serves to receive light which is emitted from the second illuminator and passes through the test piece.

The first illuminator, the light receiving device and the second illuminator may be arranged to move relative to the test piece.

The first illuminator may include a plurality of light emitting elements which are arranged in a circle and emit light of different wavelengths, the light receiving device being disposed at a center of the light emitting elements.

Selected ones of the light emitting elements may emit light of a same wavelength and be circumferentially equally spaced from each other.

Said selected ones of the light emitting elements may emit light with different phases.

According to a fourth aspect of the present invention, there is provided an optical analyzing assembly for a test piece having an obverse surface and a reverse surface, the obverse surface carrying at least one test pad, the analyzing assembly comprising:

an illuminator for illuminating the obverse surface of the test piece;

a first light receiving device for receiving light reflected on the obverse surface of the test piece; and a second light receiving device arranged below the test piece for receiving light passing through the test piece.

Other objects, features and advantages of the present invention will become clearer from the following detailed description given with reference to the accompanying drawings.

DETAILED DESCRIPTION OF THE PREFERRED EMBODIMENTS

The preferred embodiments of the present invention will be described below with reference to the accompanying drawings.

Figure 1:
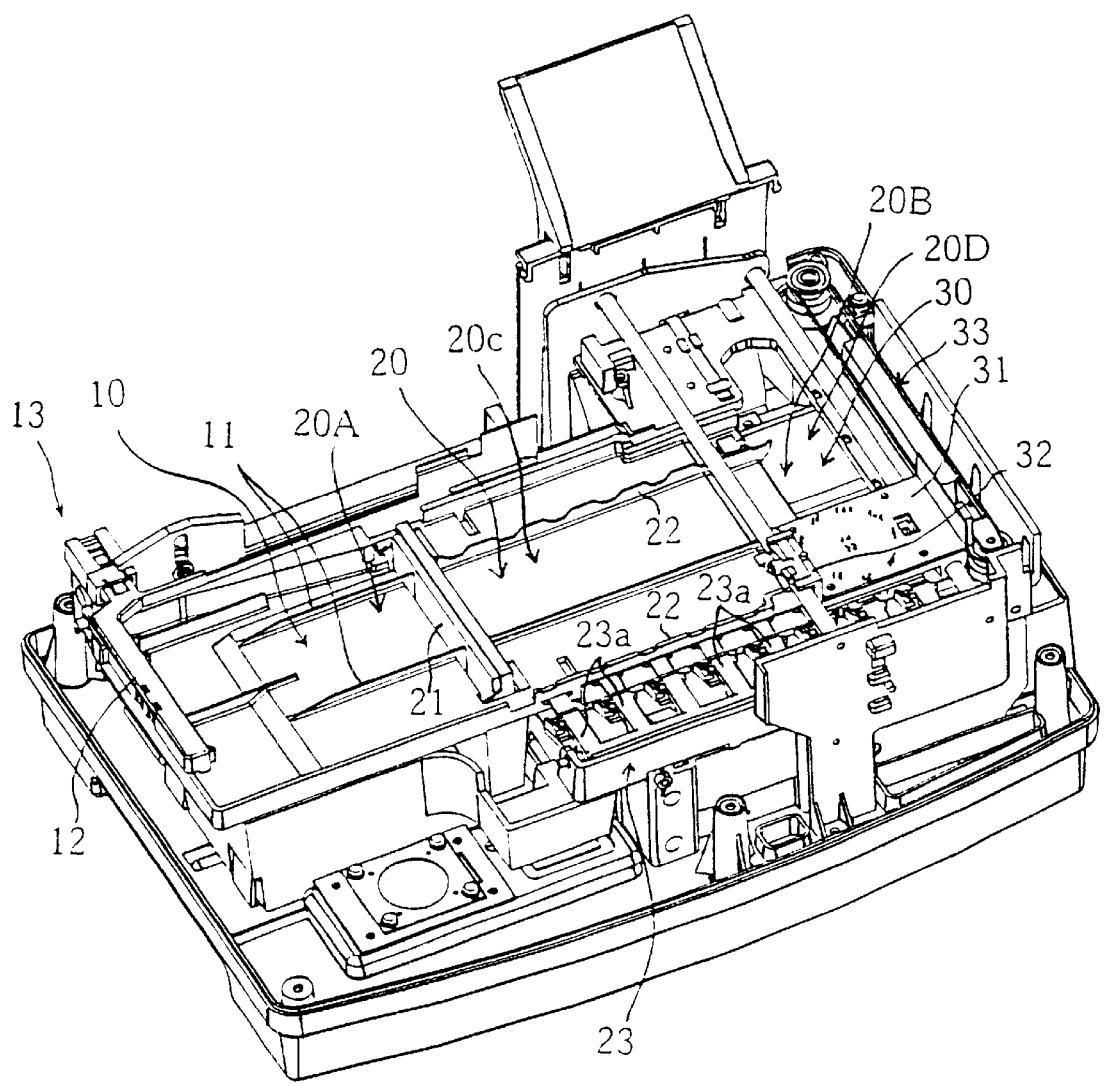
FIG. 1 is a perspective view showing a test piece analyzing apparatus according to the present invention.
Figure 2:
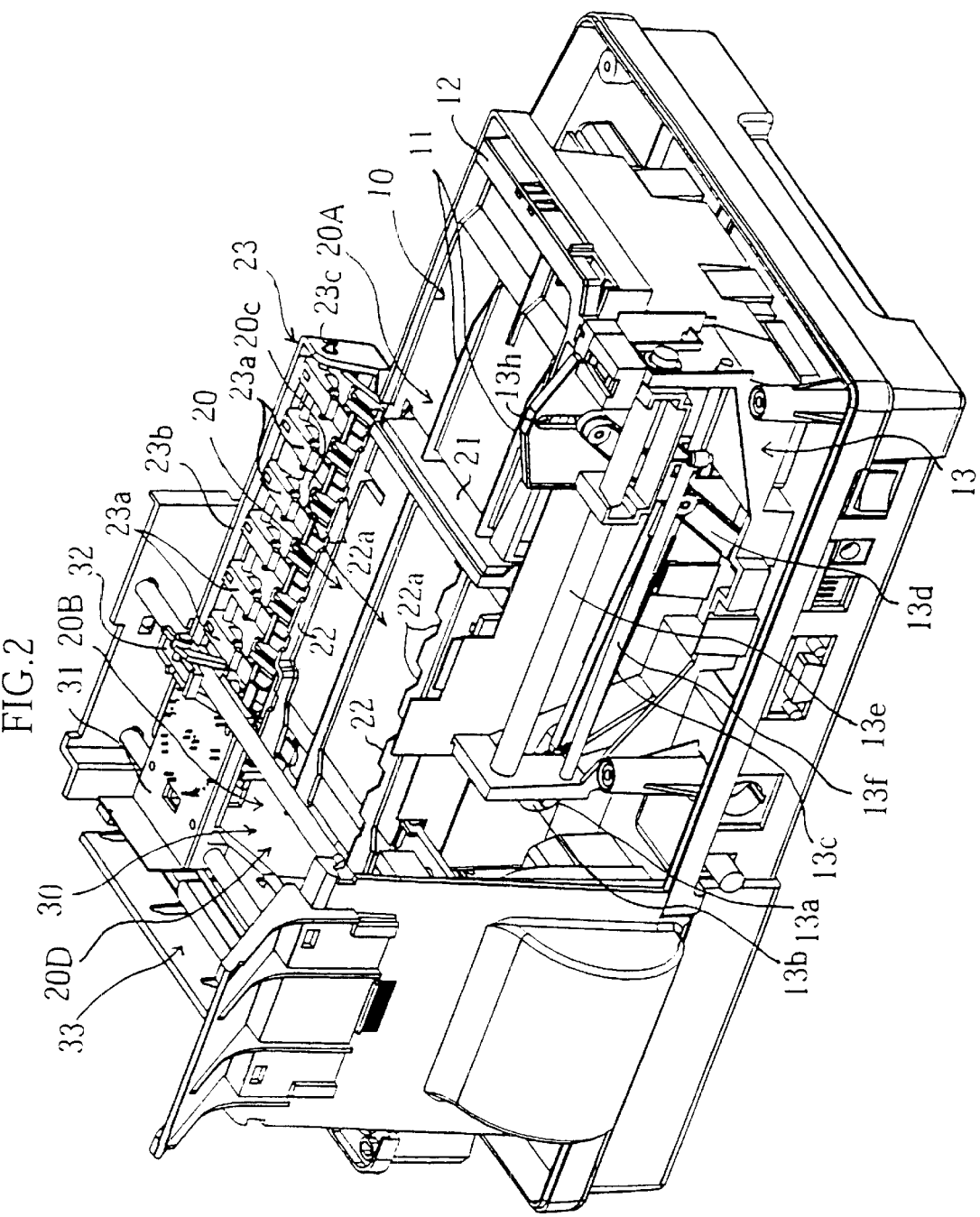
FIG. 2 shows from an different angle the test piece analyzing apparatus of FIG. 1.

Reference is first made to FIGS. 1 and 2 which are perspective views from different angles that show a test piece analyzing apparatus according to a preferred embodiment of the present invention. The illustrated analyzing apparatus is designed to automatically transfer and analyze a plurality of test pieces each of which has been dipped in a fluid specimen such as urine, blood and the like (hereinafter, such a test piece may be referred to as "wet test piece"). Each test piece is an elongated rectangular strip carrying a plurality of test pads each of which may contain a reagent and change colors when the test piece is dipped in the specimen. By analyzing the color change of each test pad, medical conditions of the specimen can be known.

The analyzing apparatus of this embodiment is provided with a test piece introducing section 10, a test piece transferring section 20 and a test piece analyzing section 30. The analyzing apparatus as a whole is controlled by a microcomputer incorporated in the analyzing apparatus. It is well known that a computer is often used for such an apparatus. Thus, in this specification, no description is given to the arrangements and operation of the microcomputer.

The test piece introducing section 10 is arranged to transfer wet test pieces one by one to the test piece transferring section 20. The test piece transferring section 20 is a region where a predetermined number of test pieces are simultaneously advanced stepwise toward the test piece analyzing section 30. In the test piece analyzing section 30, wet test pieces are analyzed by photometry. Details of these three sections will be described below.

Figure 3:
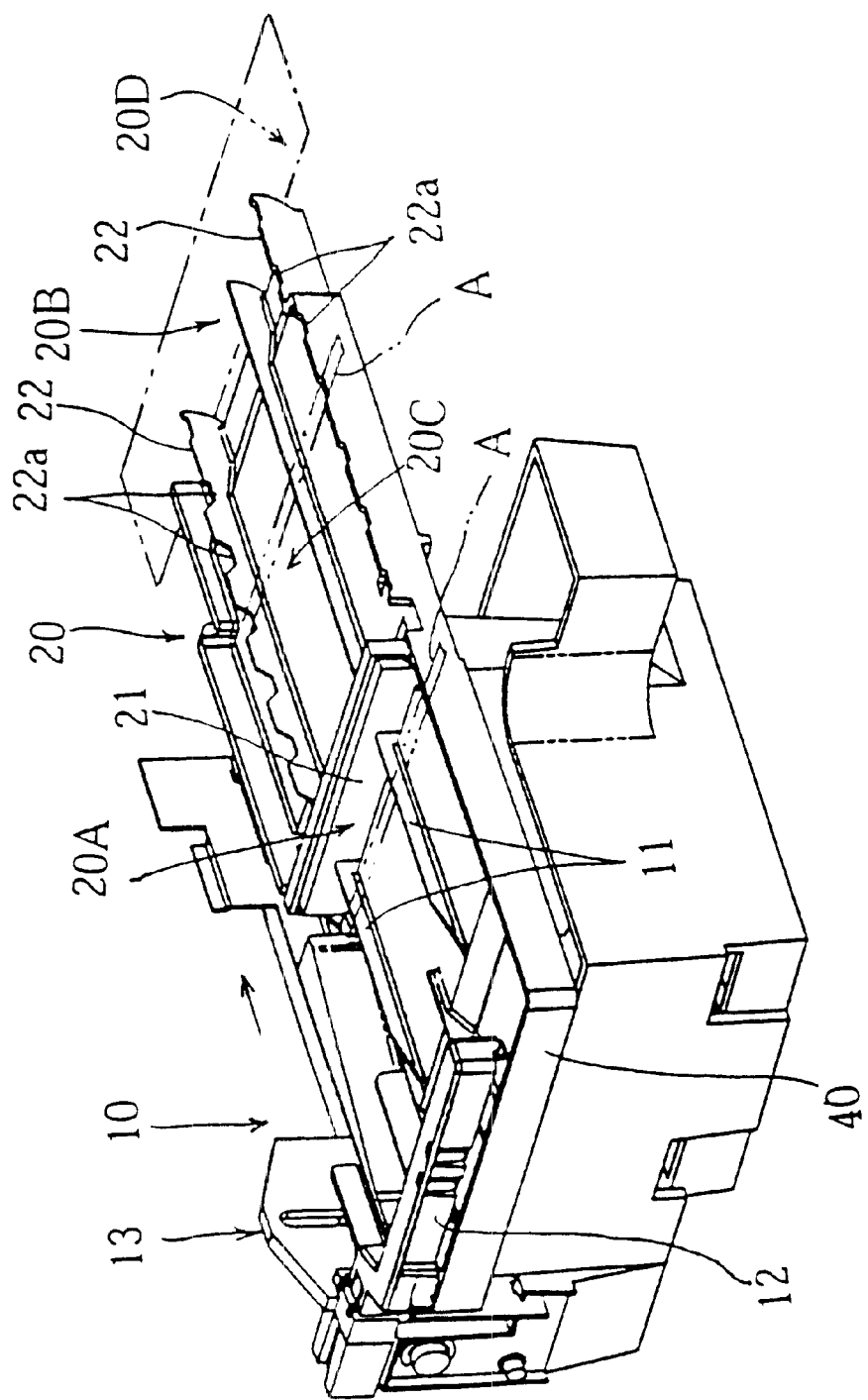
FIG. 3 is a perspective view showing principal portions of the test piece analyzing apparatus of FIG. 1.
Figure 4:
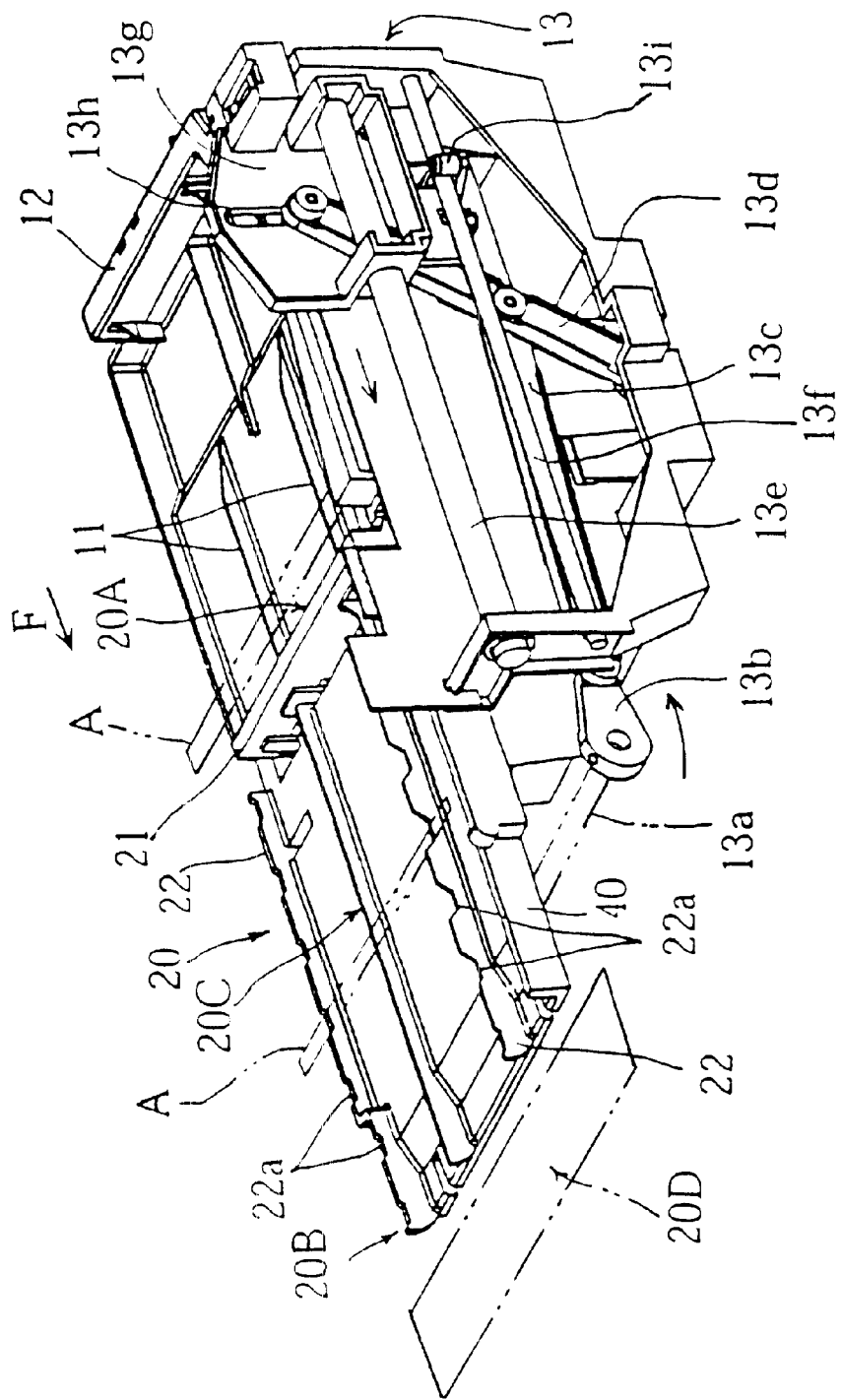
FIG. 4 shows from an different angle the principal portions of FIG. 3.

Referring to FIGS. 3 and 4, the test piece introducing section 10 and its surroundings are shown from generally opposite directions. The test piece introducing section 10 is provided with a drainage tray 40 for holding fluid specimen dripping off from test pieces A.

As illustrated, the tray 40 is long enough to extend through the test piece transferring section 20. The tray 40 includes two longitudinal side walls 22 spaced from each other in a direction perpendicular to a transfer direction F. Each of the side walls 22 has a predetermined number of hollows 22a (seven hollows in the preferred embodiment) which corresponds in position to the test piece transferring section 20. The hollows 22a in each side wall 22 are provided for holding test pieces A in place, as shown in FIG. 4. The hollows 22a are equally spaced from each other by a predetermined distance.

At the test piece introducing section 10, a pair of slide rails 11 extends horizontally in the transfer direction F. A test piece A to be analyzed is placed on the slide rails 11 in a bridging manner between the two rails. Thus, the lengthwise direction of the test piece A is perpendicular to the transfer direction F.

The test piece A (precisely, a longitudinal edge of the test piece A) is brought into contact with a movable push arm 12 and is caused to slide on the rails 11 by the push arm 12. To this end, the push arm 12 is actuated by a sliding mechanism 13.

As best shown in FIG. 4, the sliding mechanism 13 includes a rotation shaft 13a rotated by a motor 24 (see FIG. 7), a crank 13b secured to the rotation shaft 13a, a connection rod 13c, a pivot lever 13d, a primary guide shaft 13e, a secondary guide shaft 13f and a reciprocative carriage 13g.

The connection rod 13b is rotatably connected at one end to the tip of the crank 13b, while also being rotatably connected at the other end to an intermediate portion of the pivot lever 13d. The lower end of the pivot lever 13d is rotatably connected to a stationary portion of the sliding mechanism 13. The carriage 13g is slidably supported by the primary guide shaft 13e, so that the carriage 13g can reciprocate in the lengthwise directions of the shaft 13e. The carriage 13g is also guided by the secondary guide shaft 13f via a roller 13i mounted on the carriage 13g. The carriage 13g is formed with a vertically elongated opening 13h for guiding the upper end of the pivot lever 13d.

With the above arrangement, upon actuation of the motor 24 (FIG. 7) in a predetermined direction, the rotation shaft 13a and hence the crank 13b are rotated counterclockwise for example, as shown in FIG. 4. Whenever the crank 13b makes a complete turn, the pivot lever 13d is caused to move back and forth with its lower end fixed in position. As a result, the carriage 13g and hence the push arm 12 fixed thereto are caused to reciprocate in the transfer direction F and in the opposite direction while being guided by the primary and secondary guide shafts 13e, 13f.

As shown in FIG. 3, a liquid absorber 21 is provided at the inner end portion of the test piece introducing section 10. The liquid absorber 21 has a rectangular configuration elongated perpendicularly to the transfer direction F.

The liquid absorber 21 may be made of a high absorbent substance such as absorbent fiber, porous resin, macromolecular absorber or sponge. Examples of absorbent fiber may be nonwoven fabric, paper (filter paper in particular), glass fiber and cloth. It has been found that a nonwoven fabric containing acrylate fiber makes an excellent liquid absorber. Examples of porous resin may be sintered polyethylene or polyolefin and resin foam. Alternatively, use may be made of a brush-like absorber made of synthetic resin.

Figure 5:
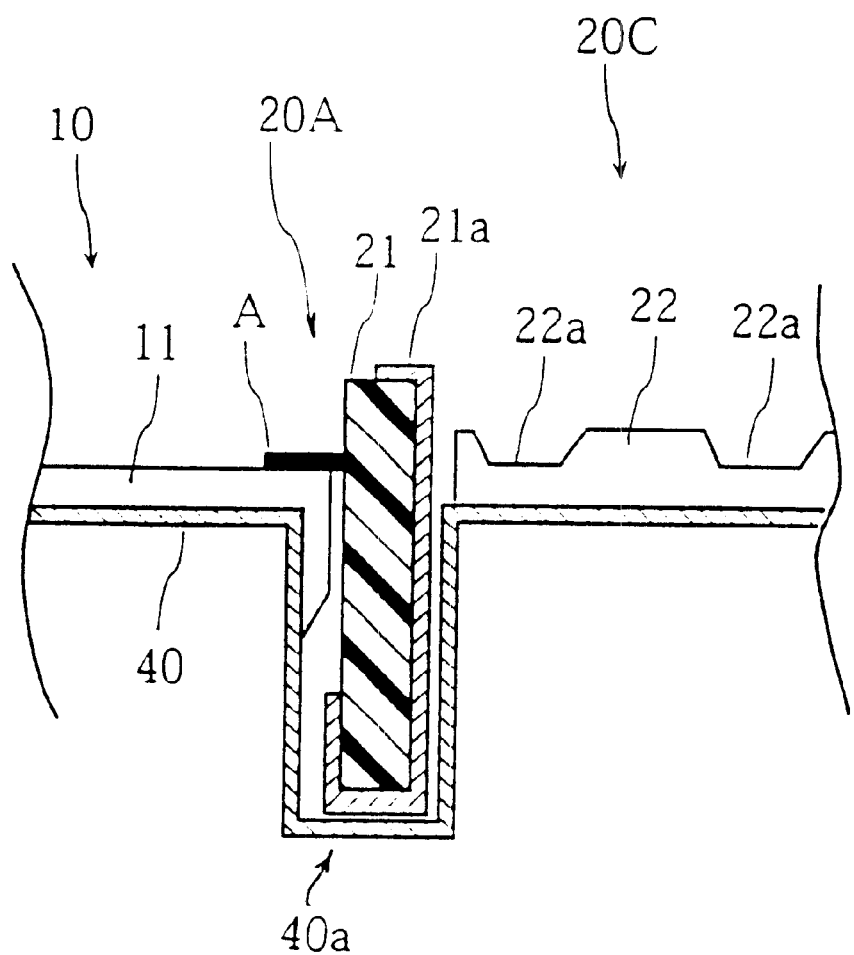
FIG. 5 is a sectional view showing a fluid absorber used in the analyzing apparatus of FIG. 1.

As shown in FIG. 5 which provides a sectional view taken along lines X—X in FIG. 1, the liquid absorber 21 is fitted in a casing 21a with its predetermined portion exposed to the exterior. The casing 21a is received in a downwardly protruding groove 40a of the tray 40. As illustrated, the height of the casing 21a is rendered greater than the depth of the groove 40a, so that the test piece A moved on the rails 11 by the push arm 12 will come into contact with the exposed portion of the liquid absorber 21a.

The casing 21a can be readily detached from the groove 40a. Thus, when the absorbing performance of the currently used liquid absorber 21 becomes unsatisfactory, it is easy to replace the absorber 21 with a new liquid absorber held in a new casing.

Referring back to FIG. 3, with the liquid absorber 21 disposed at the inner end portion of the test piece introducing section 20, a test piece A, when caused to slide 10 on the rails 11 by the push arm 12, comes into contact with the liquid absorber 21. Thereafter, the test piece A is held in this position for a while. (Hereinafter, this particular position or portion at which the test piece A is held in contact with the liquid absorber 21 may be referred to as "first waiting region", which is indicated by reference sign 20A.)

With the above arrangement, an excessive amount of the liquid specimen on the test piece A is simply absorbed by the liquid absorber 21, which is advantageous in obviating the use of a pump or any other mechanical device which may need power for actuation. Further, since the liquid absorber 21 together with the casing 21a can easily be detached from the analyzing apparatus and replaced with a new one, there is no need to wash the contaminated liquid absorber 21. In addition, the liquid absorber 21 does not need a large space for installation, which is advantageous in reducing the overall sizes of the analyzing apparatus.

The horizontal distance between the first waiting region 20A and the closest hollow 22a is rendered equal to the distance between any adjacent hollows 22a. Thus, a total of eight test pieces A (one of them is placed at the first waiting region 20A and the others are held by the hollows 22a) are to be spaced from each other in the transfer direction F by the predetermined constant distance.

As shown in FIG. 1, at the test piece transferring section 20, a horizontally reciprocative pinching mechanism 23 is provided for simultaneously transferring several test pieces A along a transfer path 20C toward the test piece analyzing section 30. Specific description will be made below with reference to FIGS. 6 and 7.

Figure 6:
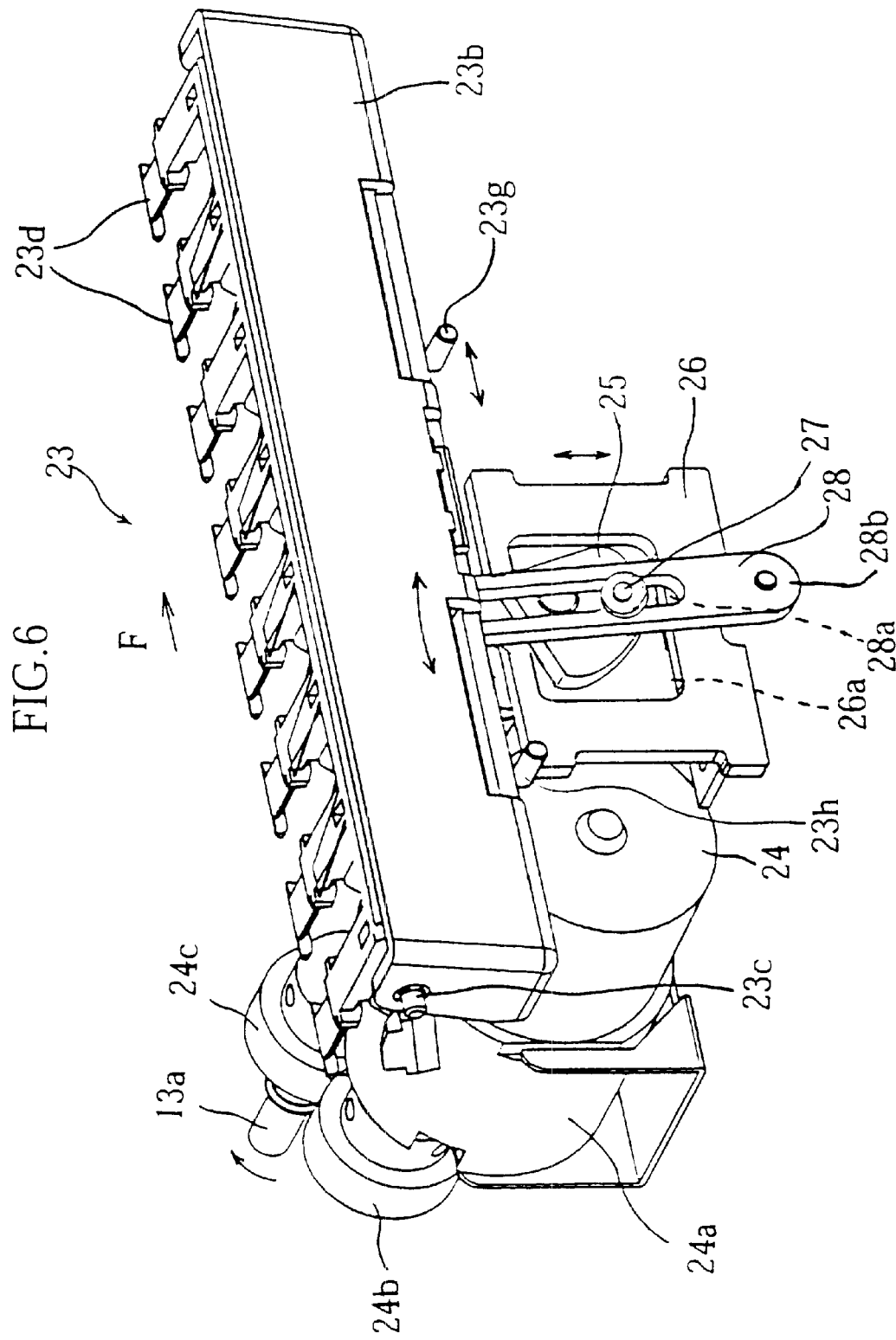
FIG. 6 is a perspective view showing a pinching mechanism incorporated in the analyzing apparatus of FIG. 1.
Figure 7:
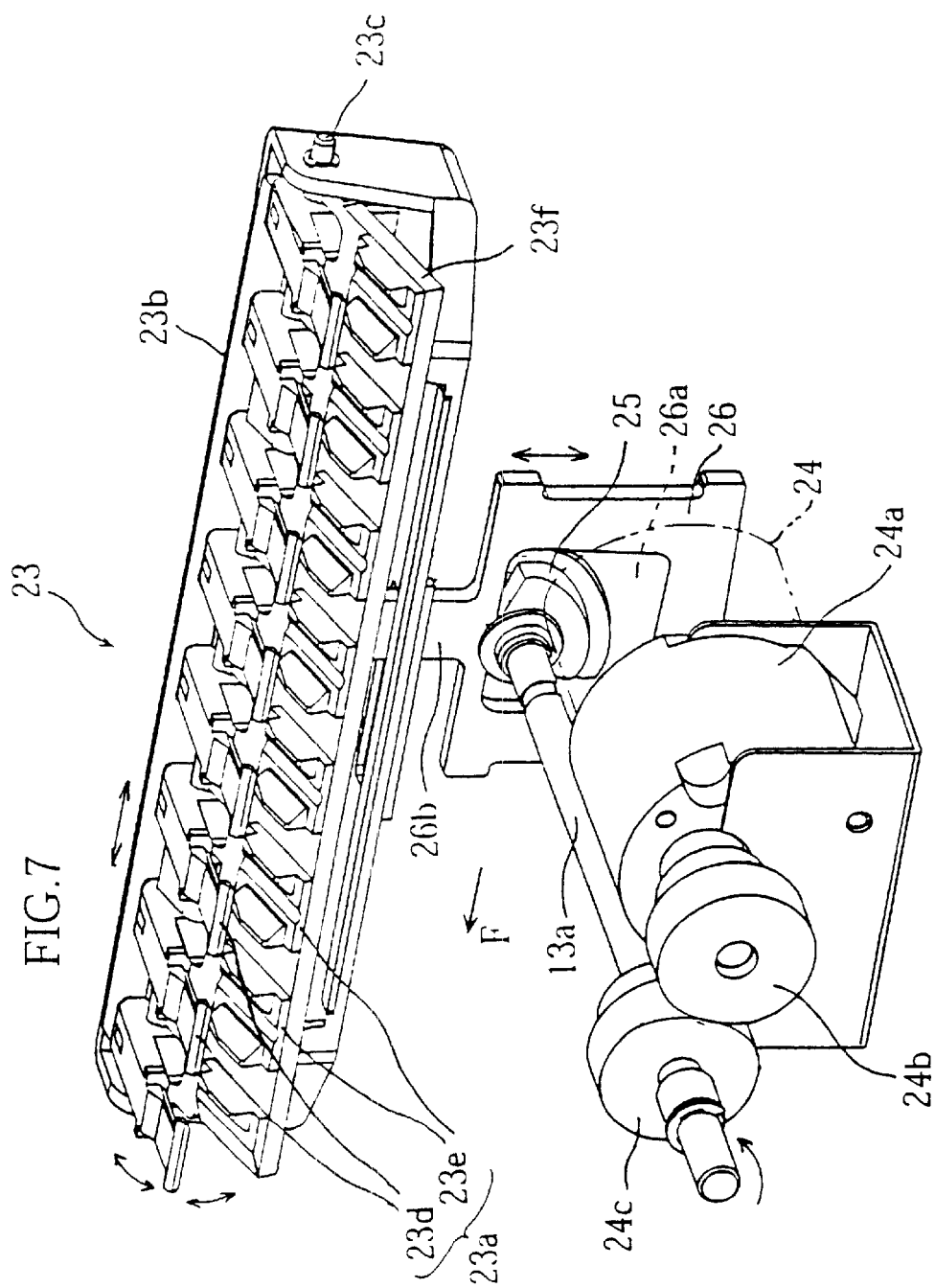
FIG. 7 shows from a different angle the pinching mechanism of FIG. 6.

As shown in FIG. 6 or 7, the pinching mechanism 23 includes a reciprocative casing 23b, a horizontal rod 23c supported by the casing 23b, and a plurality of test piece holding members 23a disposed at regular intervals corresponding to the predetermined constant distances between adjacent test piece holding members 23a.

Each of the test piece holding members 23a is made up of an upper piece 23d and a lower piece 23e cooperating with the upper piece 23d. The reciprocative casing 23b is located adjacent to one of the longitudinal side walls 22 (see FIG. 1) and arranged to be movable both in the transfer direction F and in the opposite direction, as will be described below.

The rod 23c is supported at its both ends by the casing 23c to extend in the transfer direction F. Both the upper and lower members 23d, 23e of the respective test piece holding members 23a are rotatably fitted on the rod 23c. As shown in FIG. 7, each of the upper members 23d has a free end which is suitably arranged for pressing against the upper surface of a test piece A. On the other hand, each of the lower members 23e is provided with a V-shaped portion suitable for holding a test piece A. All of the lower members 23e are attached together to a single base plate 23f.

In a ready state, each of the upper members 23d is held in a substantially horizontal position, while being urged downward by a non-illustrated elastic element such as a leaf spring. On the other hand, in the ready state, each of the lower members 23e is held in a slanting position spaced away from the corresponding upper member 23e, while being urged downward by a non-illustrated elastic element such as a coil spring.

The pinching mechanism 23 will perform a hold-and-release operation in the following manner with the aid of a vertically actuating mechanism described below.

Referring to FIG. 7, the vertically actuating mechanism shares the motor 24 with the sliding mechanism 13. The driving force of the motor 24 is transmitted to the shaft 13a via a reduction gear 24a and additional gear trains 24b, 24c. Though not shown in FIG. 7, the shaft 13a carries the previously described crank 13 at one end. At the opposite end, the shaft 13a carries a cam 25 secured thereto. The cam 25 has a generally quarter-circular configuration.

Further, the vertically actuating mechanism is provided with a cam follower 26 to be used in association with the cam 25. Specifically, the cam follower 26 includes a generally rectangular lower portion and a comparatively narrower connecting portion 26b. The lower portion is formed with a rectangular opening 26a which is rendered so large as not to restrict movement of the cam 25 accommodated in the opening 26a. The connecting portion 26b extends upward from the lower portion to come into engagement with the bottom surface of the base plate 23f.

With such an arrangement, whenever the shaft 13a makes a complete turn, the cam follower 26 is moved up and down, as indicated by a two-headed arrow. As a result, all of the lower members 23e (fixed to the base plate 23f) are caused to pivot simultaneously about the horizontal rod 23c.

As the cam follower 26 is being raised against the downwardly urging force, the lower members 23e come into contact with the upper members 23d and eventually push up the upper members 23d to a predetermined extent. Since the upper members 23d are constantly urged downward by leaf springs, test pieces A can be firmly held between the up-going lower members 23e and upper members 23d. Conversely, as the cam follower 26 is being lowered, the lower members 23e will come apart from the upper members 23d, thereby releasing the test pieces A.

While performing the hold-and-release operation described above, the pinching mechanism 23 will be moved back and forth in parallel to the transfer direction F with the aid of a horizontally actuating mechanism described below.

Referring to FIG. 6, the horizontally actuating mechanism includes a pin 27 fixed to a predetermined portion of the cam 25. The horizontally actuating mechanism also includes a swing arm 28 associated with the pin 27. The swing arm 28 is formed with an elongated opening 28a for slidably guiding the pin 27. The lower end 28b of the swing arm 28 is rotatably connected to a predetermined portion of the test piece analyzing apparatus.

In operation, the upper portion of the swing arm 28 alternately comes into pressing contact with a front engaging member 23g and a rear engaging member 23h for moving the carriage 23b in the transfer direction F and in the opposite direction, respectively. To this end, the front and rear engaging members 23g, 23h are fixed to the carriage 23b.

Figure 8:
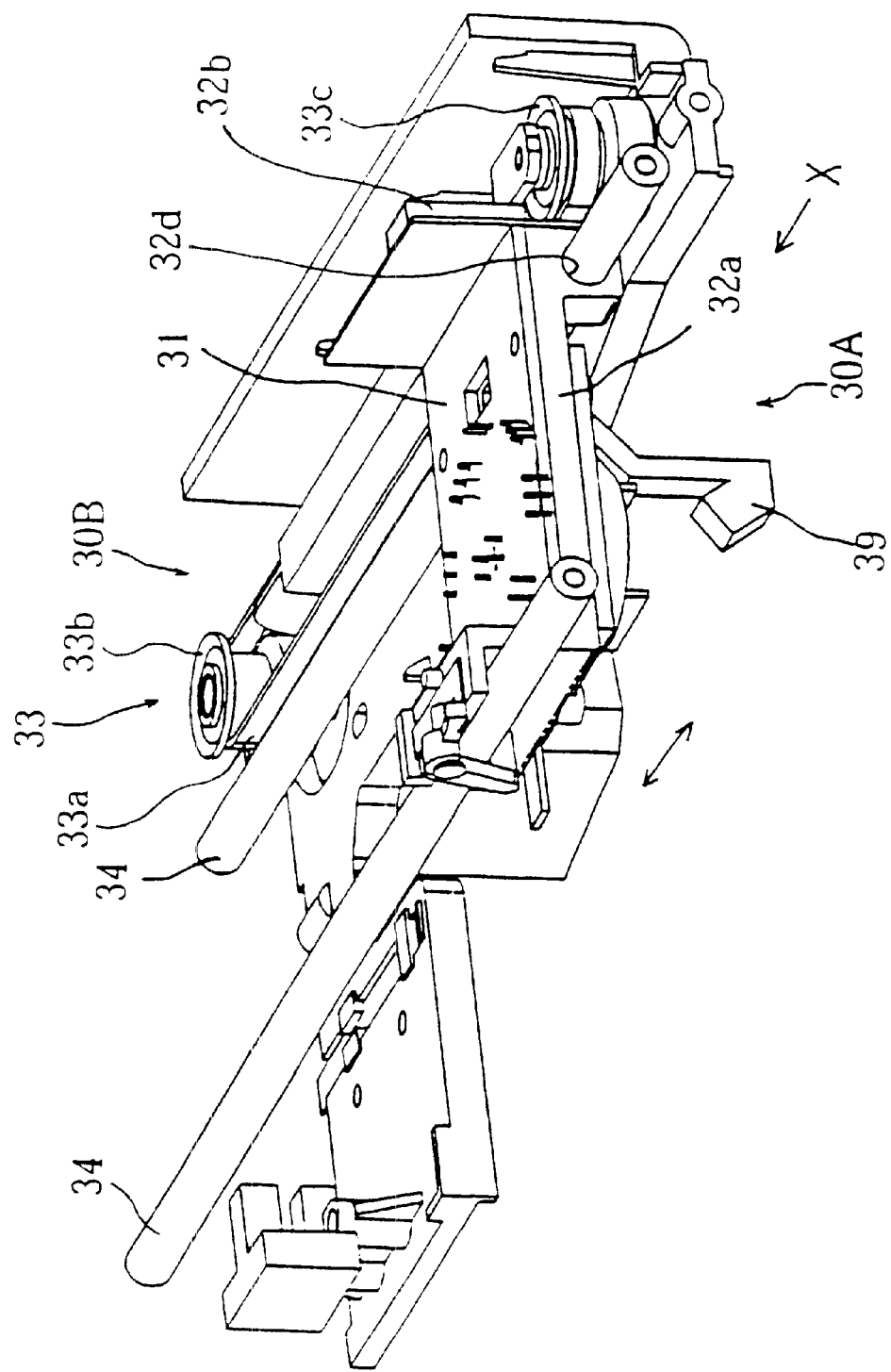
FIG. 8 is a perspective view showing an optical system incorporated in the analyzing apparatus of FIG. 1.
Figure 9:
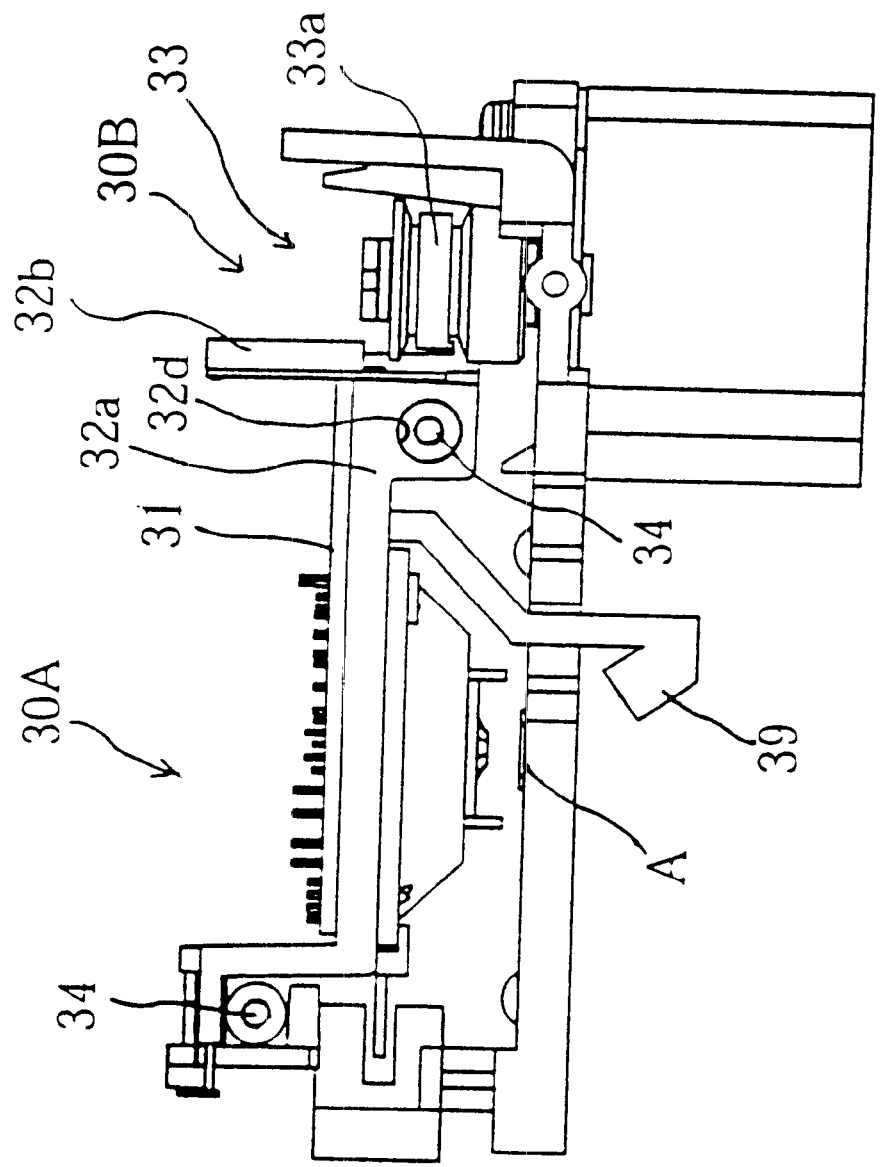
FIG. 9 is a view taken in the direction X shown in FIG. 8.

Referring now to FIGS. 8 and 9, the test piece analyzing section 30 is provided with an optical system 30A for subjecting a test piece A to an optical treatment. At the time of undergoing the optical treatment, the test piece A is held in place at a second waiting region 20B (see FIG. 1). The test piece analyzing section 30 is also provided with a driving system 30B for moving the optical system 30A longitudinally of the test piece A.

Figure 10:
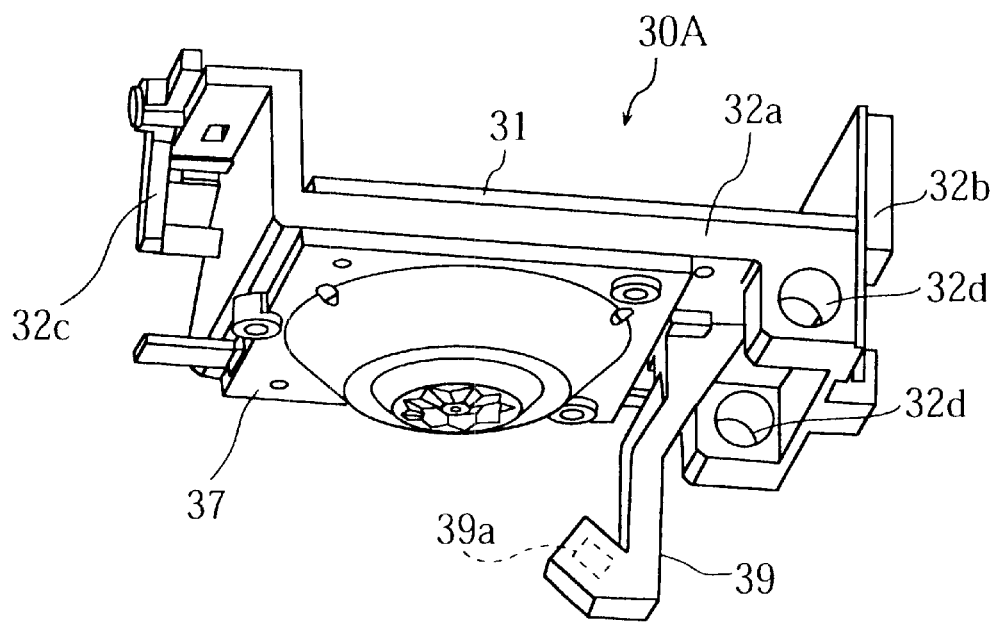
FIG. 10 is a perspective view showing an optical assembly incorporated in the analyzing apparatus of FIG. 1.
Figure 11:
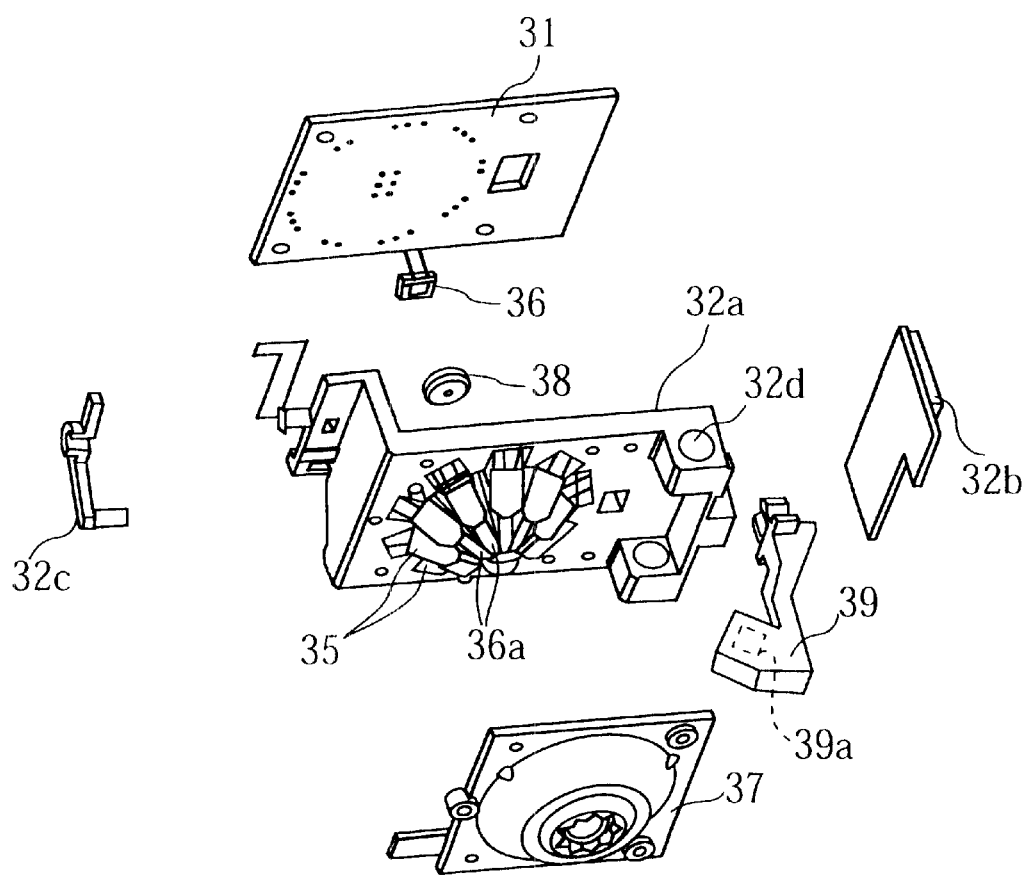
FIG. 11 is an exploded view showing principal components of the optical assembly of FIG. 10.

More specific description will now be made about the optical system 30A with additional reference to FIGS. 10 and 11. As illustrated, the optical system 30A includes an insulating substrate 31, a carriage 32a, first and second auxiliary components 32b–32c, a plurality of light emitting elements 35 (which may be referred to as "primary light emitting elements" below), a light receiving element 36, a transparent primary protection cover 37 for protecting the light emitting elements 35, a transparent secondary protection cover 38 for protecting the light receiving element 36, and an auxiliary illuminator 39 incorporating a light emitting element 39a (which may be referred to as "secondary light emitting element" below).

The substrate 31 is mounted on the carriage 32a. As shown in FIGS. 8 and 9, the carriage 32a is connected to a belt driving mechanism 33 via the first auxiliary component 32b. Specifically, the belt driving mechanism 33 includes an a endless belt 33a and a pair of pulleys 33b, 33c engaging with the endless belt 33a. Each of the pulleys 33b, 33c, or only one of them, may be driven by a non-illustrated motor for example. As can be seen from FIG. 9, the lower portion of the first auxiliary component 32b is fixed to the endless belt 33a.

The carriage 32a is supported as well as guided by a pair of parallel rods 34. One of the rods 34 extends through bores 32d (see also FIGS. 10 and 11) formed in the carriage 32a, whereas the other rod 34 extends through a clearance between the second auxiliary component 32c and the carriage 32a.

With the above arrangement, when the above-mentioned non-illustrated motor is driven in a forward or a backward direction, the carriage 32a is caused to reciprocate on the parallel rods 34 for scanning the test piece A placed at the second waiting region 20B.

The primary light emitting elements 35 may be light-emitting diodes (LEDs) arranged to generate light of different wavelengths. These elements are used for illuminate wet test pieces A from above. In the illustrated embodiment, use is made of nine light emitting elements 35 which are arranged circularly. Three of them are for emitting light of a first wavelength which may correspond to red light (R), another three elements are for emitting light of a second wavelength which may correspond to green light (G), and the remaining three elements are for emitting light of a third wavelength which may correspond to blue light (B). Three light emitting elements 35 of the same color (R, G or B) are circumferentially equally spaced from each other through about 120 degrees. Thus, the nine light emitting elements 35 are disposed alternately in circle in a repeated order of R, G and B for example.

The three light emitting elements 35 of the first wavelength (i.e., red light) are arranged to emit light with three phases which are different from each other. This fact holds for the elements 35 of the second wavelength as well as for the elements 35 of the third wavelength.

With such an arrangement, the light of the same wavelength (R, G or B) can effectively be received by the light receiving element 36.

For the light receiving element 36, use may be made of a photodiode. The light receiving element 36 is provided for detection of light reflected on the test pads of the test piece A. As viewed from below (or from above), the light receiving element 36 is positioned at the center of the circularly disposed light emitting elements 35. For preventing light emitted by the light emitting elements 35 from directly reaching the light receiving element 36, use is made of a plurality of light shielding members 36a corresponding in position to the light emitting elements 35.

Based on the light detected by the light receiving element 36, the microcomputer makes a diagnosis of each specimen and thereafter may cause a printer and/or a monitor to output the results.

The secondary light emitting element 39a in the auxiliary illuminator 39 may be an LED similar to the primary light emitting element 35. The auxiliary illuminator 39 irradiates the bottom surface of the test piece A with light having a predetermined wavelength. The light will partly penetrate the test piece A to be detected by the light receiving element 36, while being partly scattered by the test piece A. When a test pad is present on the test piece A, the light is less likely to pass through. Thus, by analyzing the light detected by the light receiving element 36, the microcomputer can determine the locations of test pads mounted on the test piece A.

In the above manner, the microcomputer can also determine the layout pattern of the test pads on the test piece A. Thus, in an instance where use is made of a plurality of test pieces having different pad layouts for different diagnostic purposes, the microcomputer can discern what diagnostic purpose each test piece is used for by judging from the particular pad pattern on the test piece.

Under the control of the microcomputer, the primary and the secondary light emitting elements may be turned on or off, as the optical system 30A is being moved longitudinally of the test piece A.

More specifically, while the optical system 30A is being moved on the parallel rods 34, primary light emitting elements 35 of the same color (red for example) are simultaneously turned on and kept powered for a predetermined period of time for illuminating the test piece A. Then, after the red-color light emitting elements 35 are turned off, the green-color light emitting elements 35 for example are turned on and then kept powered for a predetermined period of time. Similarly, after the green-color light emitting elements 35 are turned off, the blue-color light emitting elements 35 are turned on and then kept powered for a predetermined period of time. This on-off operation is performed repeatedly, and light reflected on each test pad of the test piece A is received by the light receiving element 36.

Likewise, the secondary light emitting element 39a is repeatedly turned on and off under the control of the microcomputer as the optical system 30A is being moved on the parallel rods 34.

Depending on the timing of the on-off operation of the secondary light emitting element 39a, data obtained from the light detected by the light receiving element 36 is transmitted to the microcomputer. It should be noted that the light detected by the element 36 is either the light reflected on the test piece A (that stems from the primary light emitting elements 35) or the light passing through the test piece A (that stems from the secondary light emitting element 39a). The former light (reflected on the test piece A) and the latter light (passing through the test piece A) may be detected simultaneously or with a time lag.

As compared with the light reflected on the test piece A, the light passing through the test piece A is less likely to be influenced by the specimen on the test piece A. Thus, according to the preferred embodiment, the locations of the test pads on the test piece A are accurately determined.

After the analyzing operation of the test piece A is finished, the test piece A is discarded via a discarding section 20D. To this end, the discarding section 20D is provided with an opening whose lengthwise dimension is greater than the length of the test piece A. Though not illustrated, the test piece analyzing apparatus is provided with an inner space for temporarily holding a stack of used test pieces A.

The overall operation of the test piece analyzing apparatus of the present invention will now be described below.

First, the user of the analyzing apparatus manually puts wet test pieces A, one by one, on the slide rails 11 at suitable intervals of time.

Then, the wet test piece A placed on the rails 11 is moved toward the liquid absorber 21 by the push arm 12.

Eventually, the test piece A is brought into contact with the liquid absorber 21 and stops at the first waiting region 20A (see FIG. 3) for a while. In this position, an excessive amount of the fluid specimen on the test piece A is removed (i.e., absorbed) by the liquid absorber 21.

After the test piece A comes into contact with the liquid absorber 21, the push arm 12 will be brought back to the original position by the action of the sliding mechanism 13.

Then, the test piece A at the first waiting region 20A will be transferred stepwise to come into engagement with one of the hollows 22a after another by the pinching mechanism 23. In the same manner, subsequent test pieces A are advanced by the pinching mechanism 23.

Figure 13:
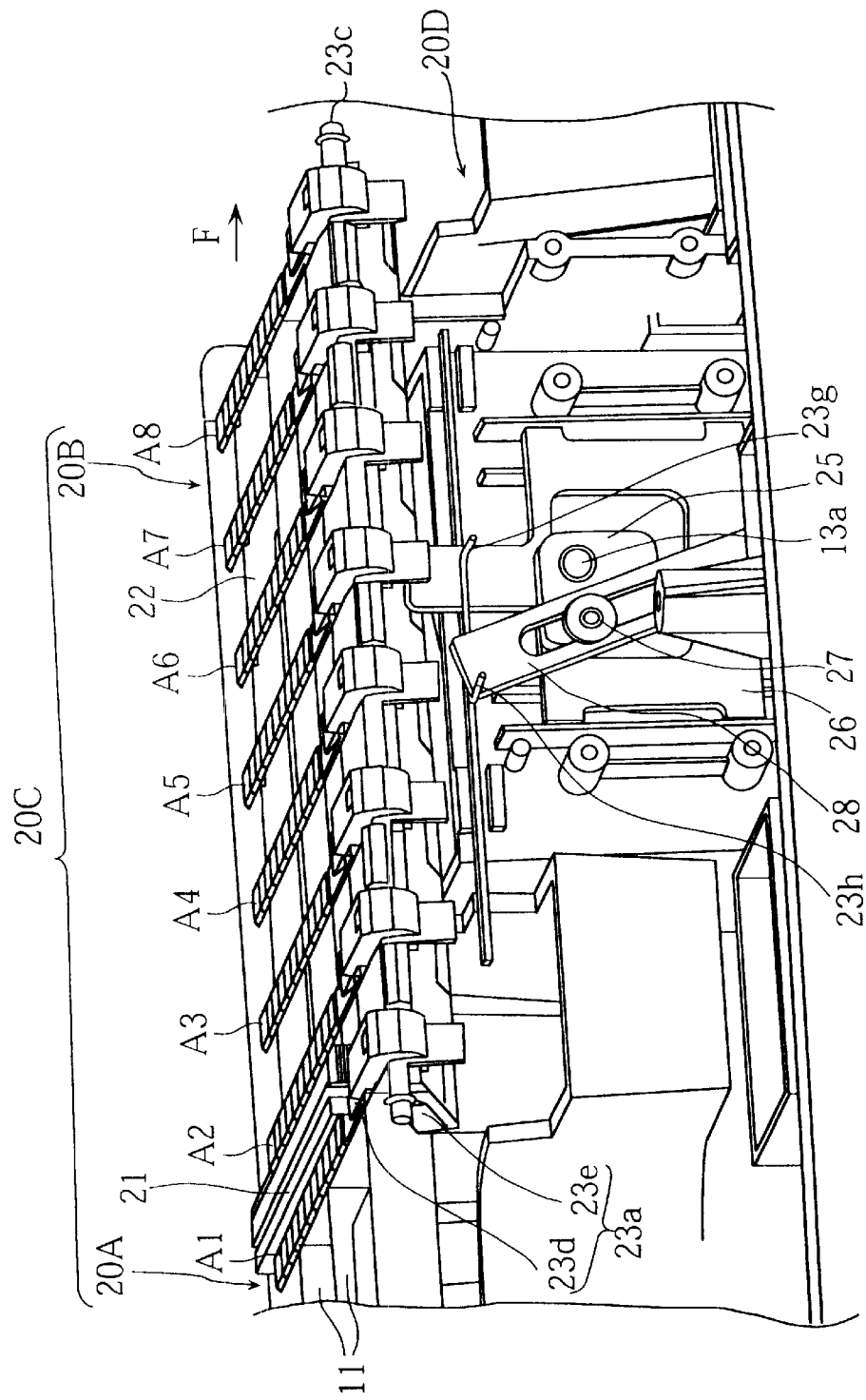
FIGS. 13–17 illustrate how a pinching mechanism of the analyzing apparatus of FIG. 1 operates in use.

At a certain stage of the transferring operation, a total of eight test pieces A1–A8 may simultaneously be held in place on the analyzing apparatus. This situation is shown in FIG. 13. As illustrated, the first test piece A1 is located at the first waiting region 20A, while the eight test piece A8 is located at the second waiting region 20B. The second to the seventh test pieces A2–A7 are disposed between the first and the eighth test pieces A1, A8. Specifically, the second test piece A2 is held in the first holding position which is the closest to the first waiting region 20A. Likewise, the third test piece A3 is held in the second holding position next to the first holding position, the fourth test piece A4 is held in the third holding position next to the second holding position, and so on. These eight test pieces A1–A8 are equally spaced from each other.

In FIG. 13, each of the test piece holding members 23a is held adjacent to a corresponding one of the test pieces A1–A8. At this time, the upper and lower members 23d, 23e of each holding member 23a are not closed (i.e., the two members 23d, 23e are spaced from each other as shown in FIG. 7).

Figure 14:
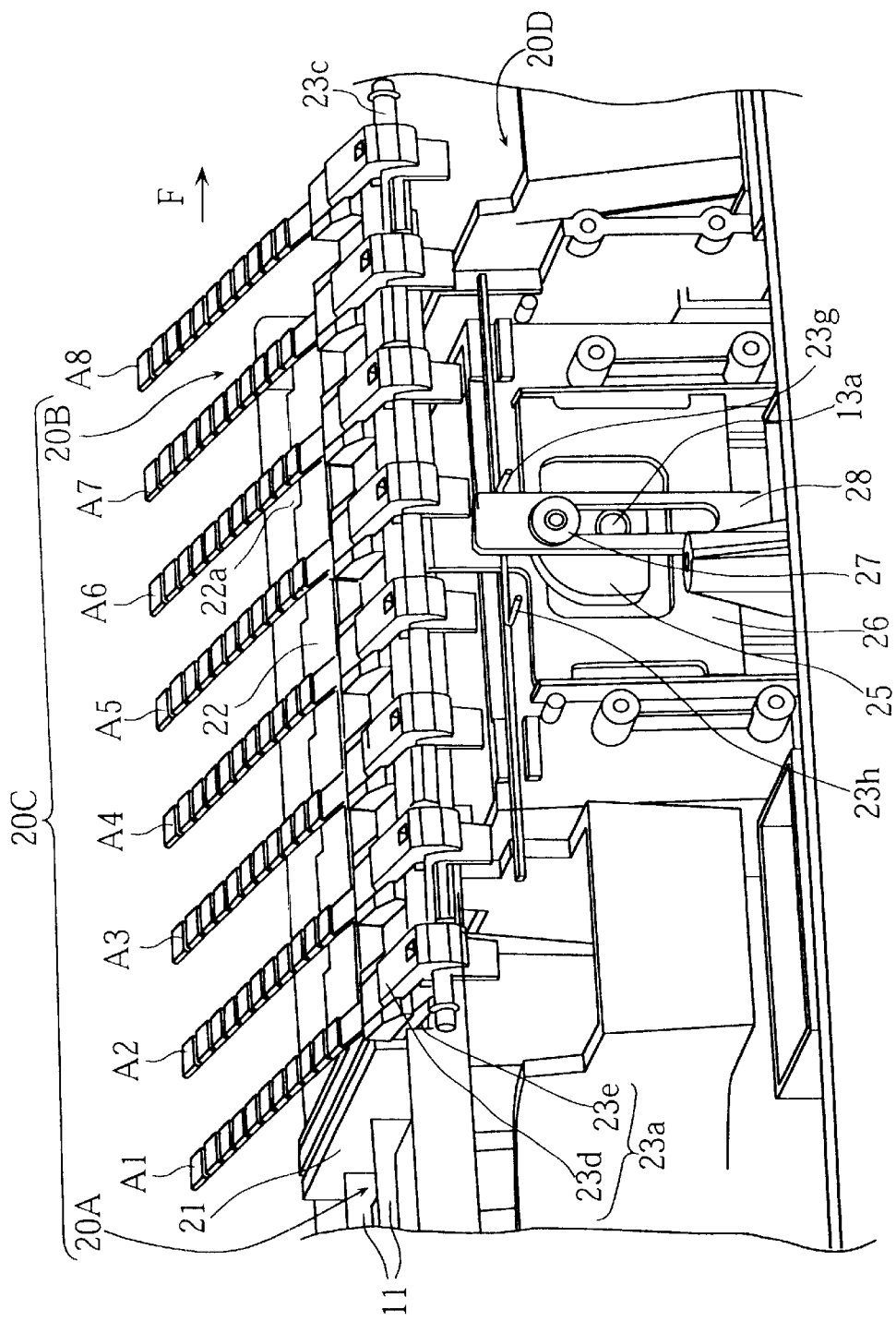

When the shaft 13a (and hence the cam 25) is rotated through about 90 degrees (first quarter rotation), as shown in FIG. 14, the cam follower 26 is displaced upward. Consequently, the test piece holding members 23a are caused to pivot upward about the the rod 23c, thereby rendering each upper and lower members 23d, 23e closed. Thus, at this stage, the first to the eighth test pieces A1–A8 are simultaneously grabbed and raised by the eight holding members 23a, respectively.

During the above first quarter rotation of the shaft 13a, the swing arm 28 is moved from a first position (FIG. 13) to a second position (FIG. 14). In the first position, the swing arm 28 inclines toward the first waiting region 20A, with its upper portion held in contact with the rear engaging member 23h. In the second position, the swing arm 28 is held upright without coming into contact with neither the rear engaging member 23h nor the front engaging member 23g. Thus, during the first quarter rotation of the shaft 13a, the pinching mechanism 23 is not moved by the swing arm 28 but remains in the initial position, as viewed in the transfer direction F.

Figure 15:
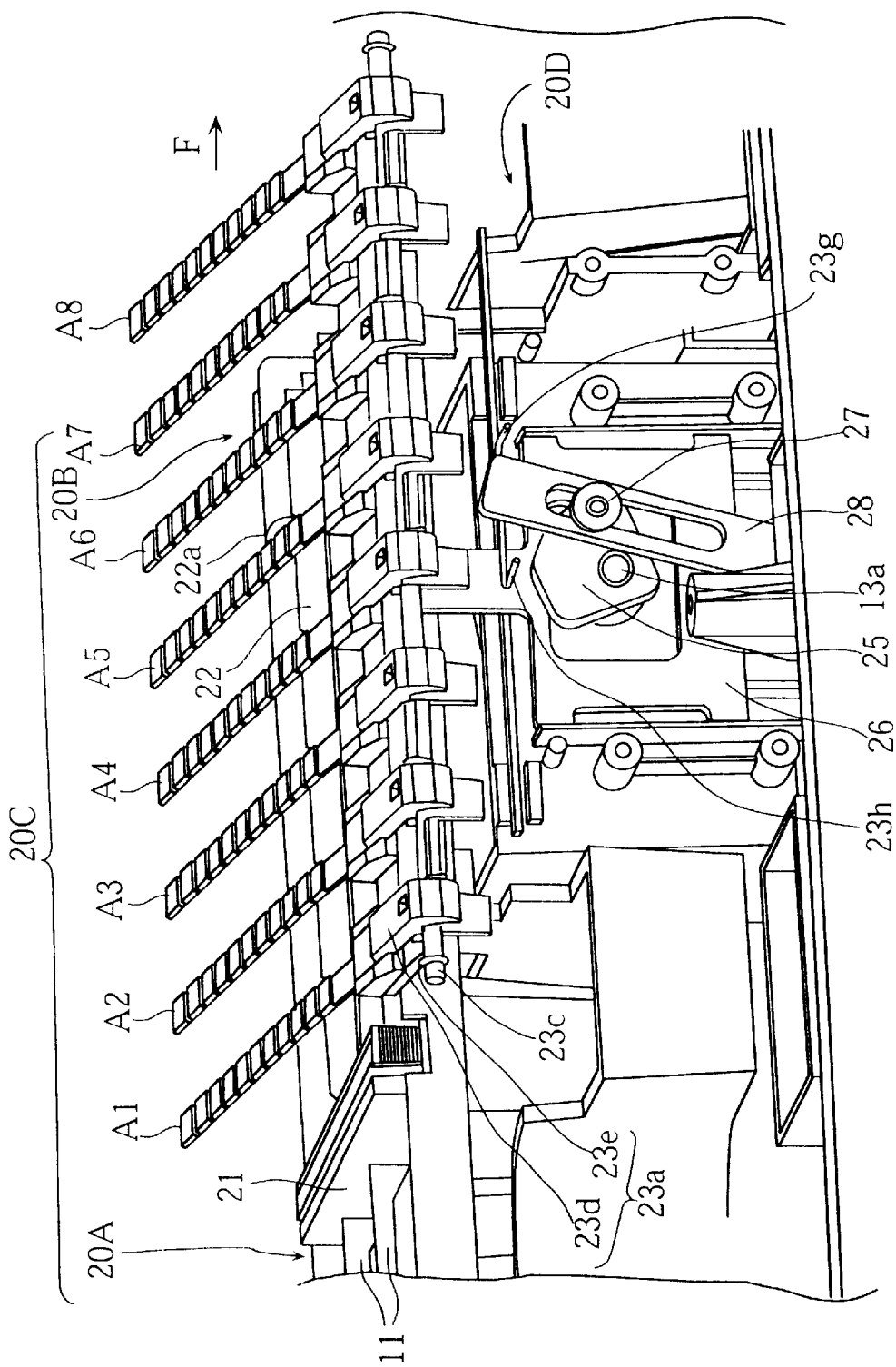

Then, when the shaft 13a is rotated through another 90 degrees (second quarter rotation), as shown in FIG. 15, the cam follower 26 is held at the same height as shown in FIG. 14 because of the particular contour of the cam 25. Thus, the respective test piece holding members A1–A8 are kept in the raised position. On the other hand, the swing arm 28 is brought into a third position in which the swing arm 28 inclines toward the second waiting region 20B.

During the above second quarter rotation, the upper portion of the swing arm 28 comes into engagement with the front engaging member 23g. Thus, in the inclining step of the swing arm 28 toward the second waiting region 20B, the pinching mechanism 23 as a whole is moved in the transfer direction F.

As a result of the above displacement of the pinching mechanism 23, the first test piece A1 (which is initially located at the first waiting region 20A) will be moved to a position right above the first holding position (in which the second test piece A2 is initially located). Likewise, the second test piece A2 will be moved to a position right above the second holding position, the third test piece A3 will be moved to a position right above the third holding position, and so on.

Figure 16:
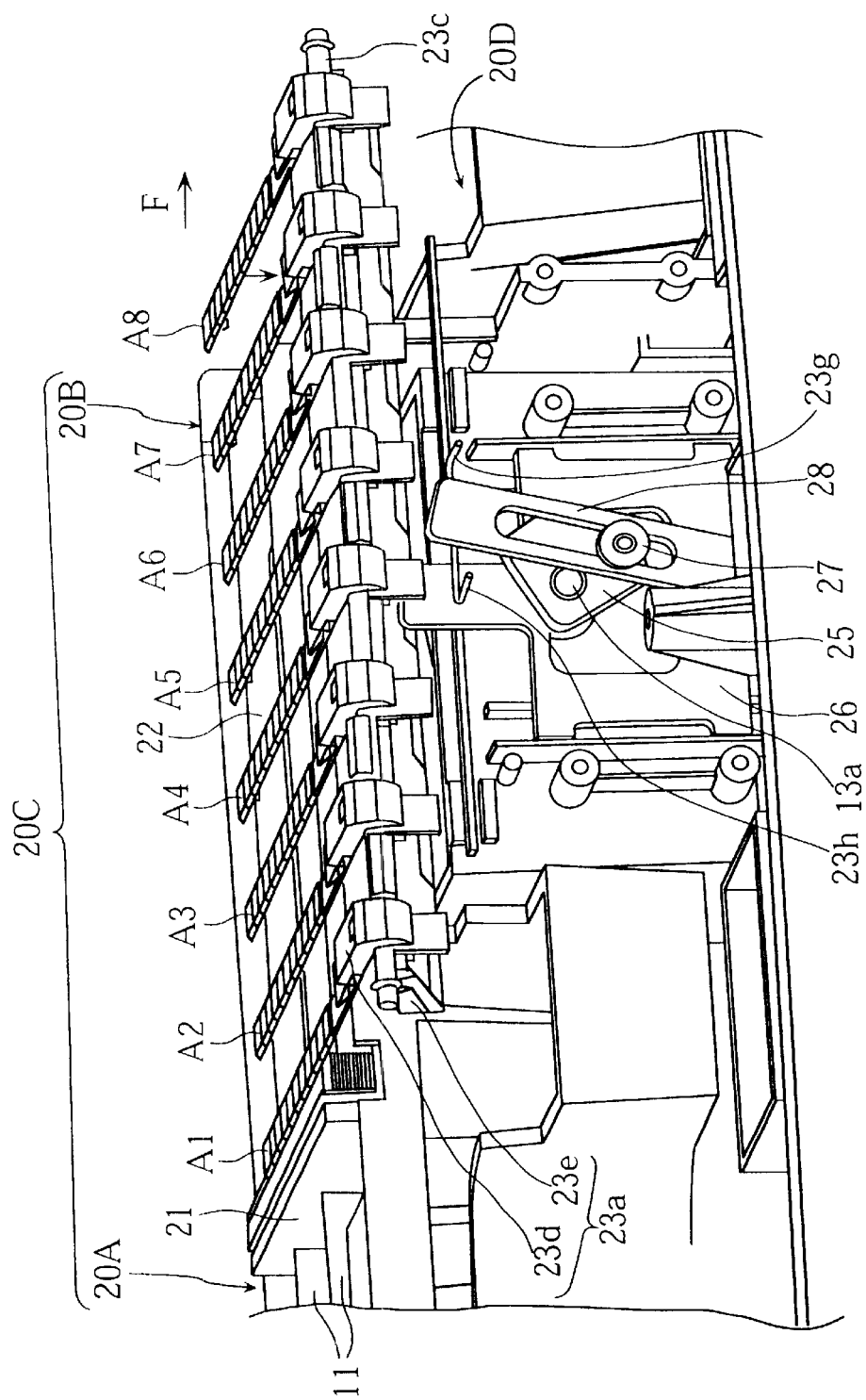

Then, when the shaft 13a is further rotated through another 90 degrees (third quarter rotation), the cam follower 26 is lowered, as shown in FIG. 16. As a result, the respective test piece holding members 23a are caused to pivot downward about the rod 23c, thereby lowering the first to the eighth test pieces A1–A8. At a suitable stage of the downward movement of the test piece holding members 23a, the upper members 23d and the corresponding lower members 23e will be opened (as shown in FIG. 7), so that the respective test pieces A1–A8 are released.

As a result, the first test piece A1 is held in place in the first holding position, the second test piece A2 in the second holding position, and so on. However, the eighth test piece A8, which has been brought to the discarding section 20D, is simply let to fall due to gravity to be discarded.

During the above third quarter rotation, the upper portion of the swing arm 28 does not engage with neither the front engaging member 23g nor the rear engaging member 23h, as shown in FIG. 16. Thus, the pinching mechanism 23 remains stationary in the transfer direction F.

Figure 17:
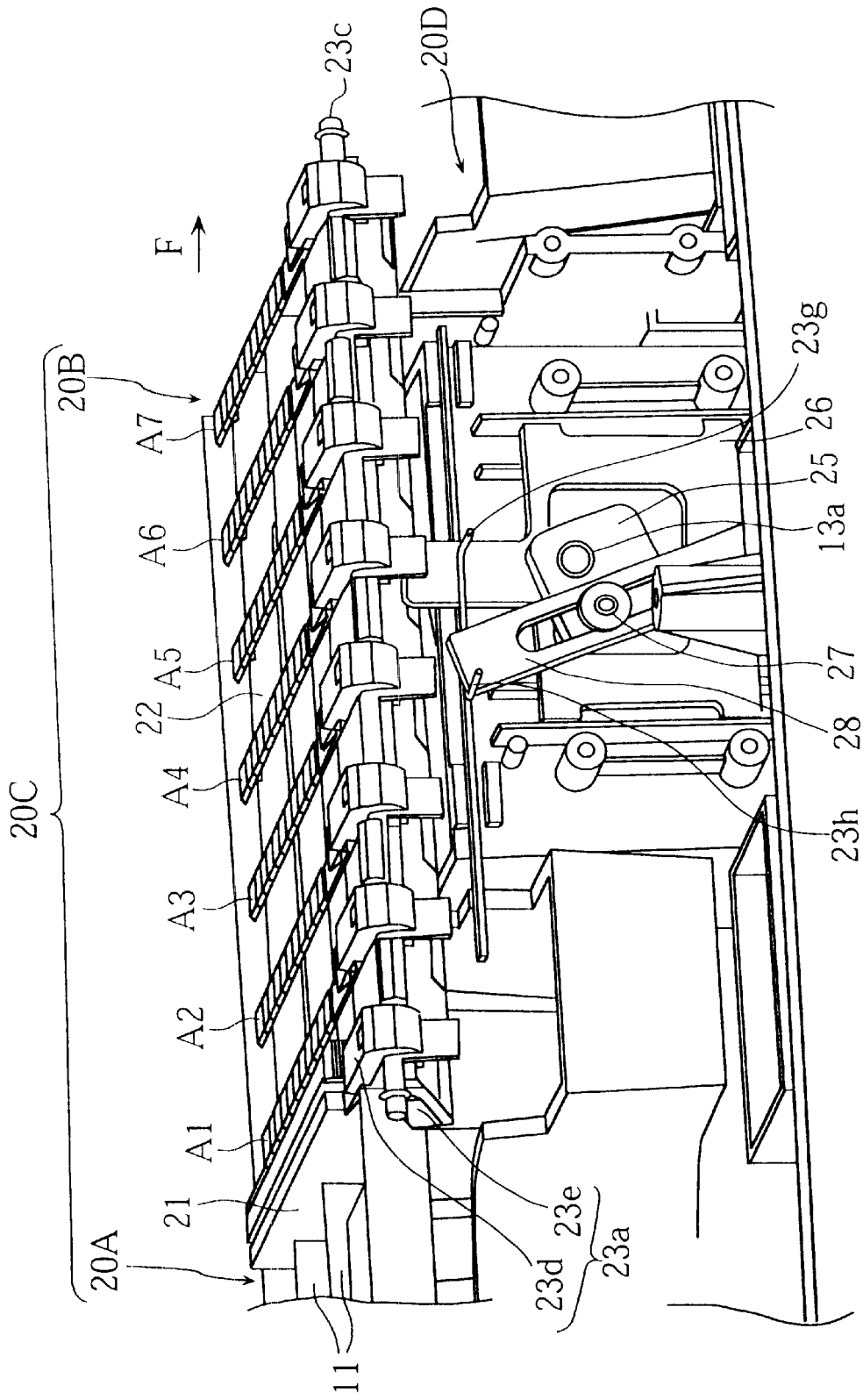

Finally, when the shaft 13a is rotated through another 90 degrees (fourth quarter rotation), as shown in FIG. 17, the cam follower 26 remains in the bottom position shown in FIG. 16. Thus, the test pieces A1–A7 are not grabbed by the holding members 23a but remain stationary.

During the fourth quarter rotation, the swing arm 28 is being inclined toward the first waiting region 20A, with its upper portion of the swing arm 28 held in contact with the rear engaging member 23h. As a result, the pinching mechanism 23 is displaced in the direction opposite to the transfer direction F, thereby bringing the respective test piece holding members 23a back to the initial position shown in FIG. 13.

Repetition of the first to the fourth quarter rotations described above causes a plurality of test pieces A to be transferred from the first waiting region 20A to the second waiting region 20B, and finally to be discarded at the discarding section 20D.

As previously stated, whenever a test piece A is brought to the second waiting region 20B, the test piece A is subjected to photometry.

With the above arrangement, each wet test piece A is displaced horizontally (i.e., in the transfer direction F) along the transfer path 20C when the wet test piece A is held in midair by the pinching mechanism 23. Thus, as opposed to the conventional apparatus, the transfer path 20C of the present invention is much less likely to be contaminated by the specimen on the test piece A.

Further, with a plurality of test piece holding members 23a, more than one test piece A can be transferred simultaneously along the transfer path 20C, which is advantageous in improving the efficiency of the test piece analyzing operation.

Still further, the shaft 13a is used for actuating the push arm 12, the cam follower 26 and the swing arm 28. Thus, it is easy to adjust the operational timing of the push arm 12, the cam follower 26 and the swing arm 28.

Figure 12:
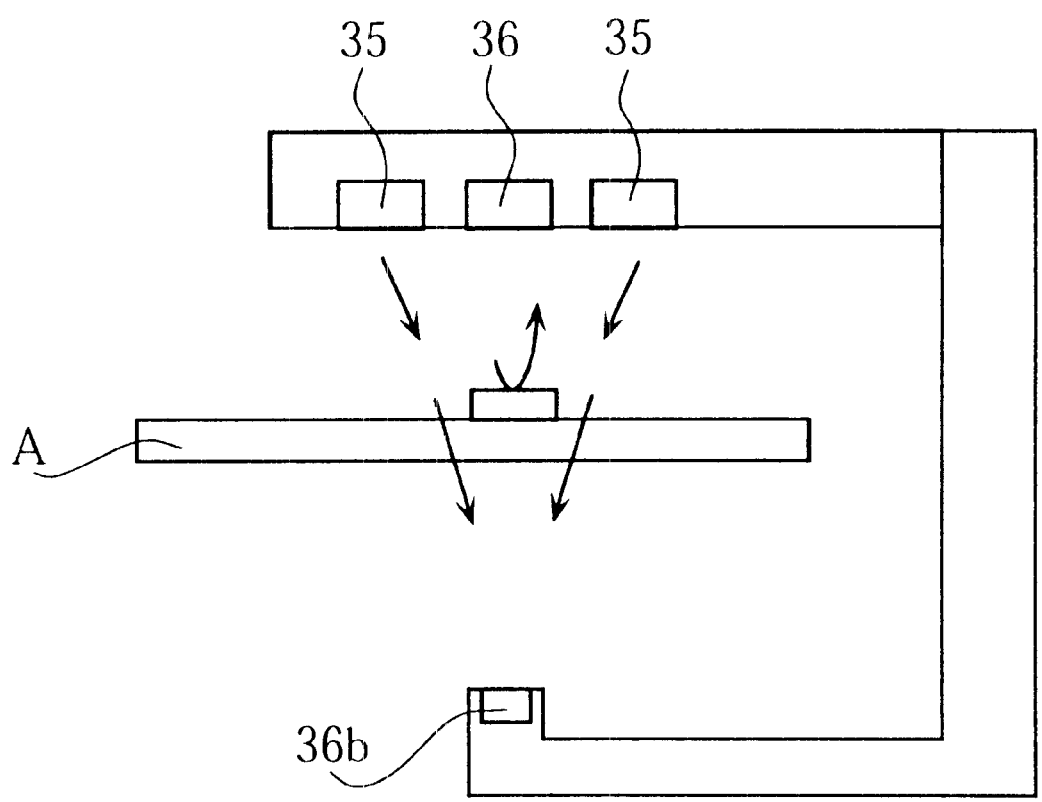
FIG. 12 is a schematic sectional view showing a modified version of the optical assembly of FIG. 10.

According to the preferred embodiment described above, arrangements are made so that the light emitted by the secondary light emitting element 39a illuminates the reverse surface of each test piece A. Alternatively, it is possible to replace the auxiliary illuminator 39 with a second light receiving device 36b arranged below the test piece A, as shown in FIG. 12. The second light receiving device 36b is provided for receiving light passing through the test piece A from its obverse surface to reverse surface. (It should be noted here that the light emitted from the light sources 35 is partly reflected or scattered by the test piece A, while partly being able to pass through the test piece A.) With such an arrangement, the same advantage can be obtained as in the preferred embodiment for precisely determining the positions of the respective test pads on the test piece A.

The present invention being thus described, it is obvious that the same may be varied in many other ways. Such variations are not to be regarded as a departure from the spirit and scope of the present invention, and all such modifications as would be obvious to those skilled in the art are intended to be included within the scope of the following claims.

What is claimed is:

1. An optical analyzing assembly for a test piece having an obverse surface and a reverse surface, the obverse surface carrying at least one test pad, the analyzing assembly comprising:
   a first illuminator for illuminating the obverse surface of the test piece;
   a light receiving device for receiving light reflected on the obverse surface of the test piece; and
   a second illuminator for illuminating the reverse surface of the test piece for locating the test pad;
   wherein the light receiving device also serves to receive light which is emitted from the second illuminator and passes through the test piece.

2. The optical analyzing assembly according to claim 1, wherein the first illuminator, the light receiving device and the second illuminator are arranged to move relative to the test piece.

3. The optical analyzing assembly according to claim 1, wherein the first illuminator includes a plurality of light emitting elements which are arranged in a circle and emit light of different wavelengths, the light receiving device being disposed at a center of the light emitting elements.

4. The optical analyzing assembly according to claim 3, wherein selected ones of the light emitting elements emit light of a same wavelength and are circumferentially equally spaced from each other.

5. The optical analyzing assembly according to claim 4, wherein said selected ones of the light emitting elements emit light with different phases.

6. An optical analyzing assembly for a test piece having an obverse surface and a reverse surface, the obverse surface carrying at least one test pad, the analyzing assembly comprising:

an illuminator for illuminating the obverse surface of the test piece;

a first light receiving device for receiving light reflected on the obverse surface of the test piece; and a second light receiving device arranged below the test piece for receiving light passing through the test piece.

* * * * *